(12) United States Patent
Naidu

(10) Patent No.: US 12,605,096 B2
(45) Date of Patent: Apr. 21, 2026

(54) INTEGRATED INTRAVENOUS CATHETER HAVING A SIDE PORT FOR FACILITATING BLOOD DRAW

(71) Applicant: Becton, Dickinson and Company, Franklin Lakes, NJ (US)

(72) Inventor: Jithendra Kumar Sathyanarayana Naidu, Woodlands (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1096 days.

(21) Appl. No.: 17/143,979

(22) Filed: Jan. 7, 2021

(65) Prior Publication Data

US 2021/0228126 A1      Jul. 29, 2021

Related U.S. Application Data

(60) Provisional application No. 62/967,484, filed on Jan. 29, 2020.

(51) Int. Cl.
| | |
|---|---|
| *A61B 5/15* | (2006.01) |
| *A61M 25/00* | (2006.01) |
| *A61M 39/10* | (2006.01) |
| *A61M 39/28* | (2006.01) |

(52) U.S. Cl.
CPC .. *A61B 5/150992* (2013.01); *A61B 5/150213* (2013.01); *A61B 5/150221* (2013.01); *A61M 25/0084* (2013.01); *A61M 39/105* (2013.01); *A61M 2025/0089* (2013.01); *A61M 2039/1072* (2013.01); *A61M 2039/1077* (2013.01); *A61M 39/28* (2013.01)

(58) Field of Classification Search
CPC ........ A61B 5/150992; A61B 5/150213; A61B 5/150221; A61M 2039/1072; A61M 2039/1077; A61M 25/0084; A61M 39/105
See application file for complete search history.

(56) References Cited

U.S. PATENT DOCUMENTS

| | | | |
|---|---|---|---|
| 4,169,548 A | 10/1979 | Bond | |
| 5,769,871 A | * 6/1998 | Mers Kelly | ........... A61M 25/10 |
| | | | 606/198 |
| 8,267,375 B1 | 9/2012 | Lahousse et al. | |

(Continued)

FOREIGN PATENT DOCUMENTS

| | | |
|---|---|---|
| CN | 205549189 U | 9/2016 |
| CN | 110214034 A | 9/2019 |

(Continued)

OTHER PUBLICATIONS

"Septum Definition & Meaning." Merriam-Webster, Merriam-Webster, Apr. 22, 2009, www.merriam-webster.com/dictionary/septum. (Year: 2009).*

*Primary Examiner* — Jacqueline Cheng
*Assistant Examiner* — Jairo H Portillo
(74) *Attorney, Agent, or Firm* — Kirton McConkie; Whitney Blair; Kevin Stinger

(57) ABSTRACT

Integrated IV catheters can have a side port that facilities drawing blood. The side port provides separate fluid pathways for drawing blood and for injecting fluids via an extension set. The side port can be configured to allow the extension set to be primed while a blood sample is collected. In this way, the collection of a blood sample at the time of catheter insertion is facilitated.

17 Claims, 15 Drawing Sheets

(56)                References Cited

U.S. PATENT DOCUMENTS

| | | | |
|---|---|---|---|
| 2003/0170308 A1 | 9/2003 | Cleary et al. | |
| 2012/0016213 A1* | 1/2012 | Burkholz ........... | A61B 5/15003 |
| | | | 422/68.1 |
| 2013/0324975 A1* | 12/2013 | Douglas .............. | A61M 39/283 |
| | | | 604/328 |
| 2014/0188002 A1* | 7/2014 | Close ............... | A61B 5/150992 |
| | | | 600/581 |
| 2014/0309551 A1* | 10/2014 | Burkholz ......... | A61B 5/150213 |
| | | | 600/573 |
| 2015/0038910 A1* | 2/2015 | Harding ................ | A61M 39/10 |
| | | | 604/167.02 |
| 2019/0021640 A1* | 1/2019 | Burkholz .............. | A61M 39/12 |
| 2019/0321599 A1* | 10/2019 | Burkholz .............. | A61M 25/02 |
| 2019/0374144 A1* | 12/2019 | Langdell .......... | A61B 5/150648 |
| 2020/0016374 A1 | 1/2020 | Burkholz et al. | |

FOREIGN PATENT DOCUMENTS

| | | |
|---|---|---|
| CN | 212593351 U | 2/2021 |
| EP | 0376168 A2 | 7/1990 |
| EP | 2153865 | 2/2010 |
| WO | 94/12093 | 6/1994 |
| WO | 9858989 A1 | 12/1998 |
| WO | 2008/058132 | 5/2008 |
| WO | 2008/058133 | 5/2008 |
| WO | 2008132045 A2 | 11/2008 |
| WO | 2020/018497 | 1/2020 |

* cited by examiner

INTEGRATED INTRAVENOUS CATHETER HAVING A SIDE PORT FOR FACILITATING BLOOD DRAW

RELATED APPLICATIONS

This application claims the benefit of U.S. Provisional Patent Application No. 62/967,484, filed Jan. 29, 2020, and entitled INTEGRATED INTRAVENOUS CATHETER HAVING A SIDE PORT FOR FACILITATING BLOOD DRAW, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter ("PIVC"). As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into the vasculature of the patient.

An integrated PIVC is a PIVC having an integrated extension set. Such extension sets typically consist of extension tubing that is integrated at one end into the catheter adapter and that includes an access port (e.g., a luer connector) coupled to the other end. Integrated PIVCs are oftentimes used to draw blood. For example, after inserting the catheter of the integrated PIVC into the patient's vasculature, a clinician may allow blood to flow into the extension set up to the access port. To enable this blood flow, a vent plug will typically be coupled to the access port, which will allow air to escape the extension tube as the blood flows into the extension tube. Once the blood has flowed up to the access port, the clinician will then remove the vent plug and attach a blood collection set (e.g., a vacuum tube adapter) in its place. The blood can then be collected.

The process of collecting blood through the extension set of an integrated PIVC has various drawbacks. For example, before blood can be collected, the entire extension set must be primed (i.e., air must be vented from the access port to allow blood to flow into the extension set up to the access port). Additionally, the removal of the vent plug from the access port exposes the fluid pathway to the external environment. The subsequent attachment of the blood collection set could therefore contaminate the fluid pathway. As a result, the clinician may need to sterilize the access port before attaching the blood collection set thereby prolonging the blood collection process. Due to the length of the extension tubing, it can take a substantial amount of time for the blood to flow into the blood collection set, particularly when the patient's blood pressure is low. Once blood is collected, there will be residual blood within the extension set. Although fluid could be injected through the access port to flush the blood from the extension tubing, it is difficult to fully flush residual blood that may be trapped within the access port. This residual blood could increase the risk of bloodstream infection (BSI) since the same access port is also typically used to inject fluids into the patient's vasculature.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to integrated IV catheters including PIVCs that have a side port that facilities drawing blood. The side port provides separate fluid pathways for drawing blood and for injecting fluids via an extension set. The side port can be configured to allow the extension set to be primed while a blood sample is collected. In this way, the collection of a blood sample at the time of catheter insertion is facilitated.

In a first set of example embodiments, an integrated IV catheter, such as a PIVC, may include a catheter adapter, a side port and an extension set. The catheter adapter includes a catheter that inserts into a patient's vasculature. The side port has a distal end by which the side port is connected to the catheter adapter, a proximal end and a side branch. The extension set is connected to the side port via the side branch. The proximal end of the side port provides a first fluid pathway for drawing blood from the patient's vasculature and the side branch of the side port provides a second fluid pathway for injecting fluids into the patient's vasculature.

In the first set of example embodiments, the side port may include a septum that is positioned at the proximal end in the first fluid pathway. A blood collection set may be inserted through the septum and may be configured to vent air from the first fluid pathway. Alternatively, a blood collection adapter may be coupled to the proximal end of the side port and may extend though the septum. The blood collection adapter can be configured to vent air from the first fluid pathway.

In the first set of example embodiments, the septum may be included in an active septum valve that is configured to move from a closed position in which the septum blocks the second fluid pathway and an open position in which the septum does not block the second fluid pathway. The septum may include venting channels that vent air from the second fluid pathway when the active septum valve is in the closed position. The active septum valve may include an actuating member having one or more tabs that interface with the side port to prevent the active septum valve from being moved from the open position to the closed position. In such cases, for each of the one or more tabs, the side port may include a distal slot in which the tab is inserted when the active septum valve is in the closed position and a proximal slot in which the tab is inserted when the active septum valve is in the open position. The distal slot may be configured to allow the tab to slide proximally out of the distal slot, while the proximal slot may be configured to prevent the tab from sliding distally out of the proximal slot.

In the first set of example embodiments, the side port may further include a venting membrane that is positioned between the side branch and the proximal end of the side port. The active septum valve may be configured to allow air contained in the extension set to escape through the venting membrane with the active septum valve is in the closed position.

In the first set of example embodiments, when the side port includes an active septum valve, a blood collection adapter may be connected to the proximal end of the side port and may prevent the active septum valve from moving to the open position.

In a second set of example embodiments, an integrated PIVC may include one or more of the following: a catheter adapter having a catheter that is configured to be inserted into a patient's vasculature; a side port having a distal end by which the side port is connected to the catheter adapter, a proximal end housing an active septum valve and a side branch; and an extension set that is connected to the side port via the side branch.

In the second set of example embodiments, the active septum valve may include a septum and may be configured to move from a closed position in which the septum blocks a fluid pathway through the side branch to an open position in which the septum does not block the fluid pathway through the side branch. The septum may be configured to vent air from the extension set when the active septum valve is in the closed position.

In the second set of example embodiments, the integrated PIVC may also include a blood collection adapter that is connected to the proximal end of the side port. The blood collection adapter can provide a separate fluid pathway for drawing blood when the active septum valve is in the closed position. The blood collection adapter may prevent the active septum valve from moving to the open position.

In a third set of example embodiments, an integrated PIVC may include a catheter adapter having a catheter that is configured to be inserted into a patient's vasculature, a side port and an extension set. The side port has a distal end by which the side port is connected to the catheter adapter. The side port also has a proximal end housing an active septum valve. The side port further has a side branch. The active septum valve includes a septum and is configured to move from a closed position in which the septum blocks a first fluid pathway through the side branch and an open position in which the septum does not block the first fluid pathway. The proximal end provides a second fluid pathway through which blood can be drawn from the patient's vasculature while the active septum valve is in the closed position. The extension set is connected to the side port via the side branch and has an access port by which a fluid can be injected into the patient's vasculature via the first fluid pathway.

In the third set of example embodiments, the integrated PIVC may also include a blood collection adapter that is coupled to the proximal end of the side port. The septum may be configured to vent air from the extension set when the active septum valve is in the closed position to thereby enable the extension set to be primed while the active septum valve is in the closed position.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

4

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Embodiments of the present disclosure will primarily be described in the context of integrated PIVCs. However, embodiments of the present disclosure equally extend to other integrated IV catheters. Accordingly, the techniques of the present disclosure can be applied to any type of integrated IV catheter. For purposes of the specification and the claims, an integrated IV catheter should be construed as an IV catheter that includes an integrated extension set.

Figure 1A:
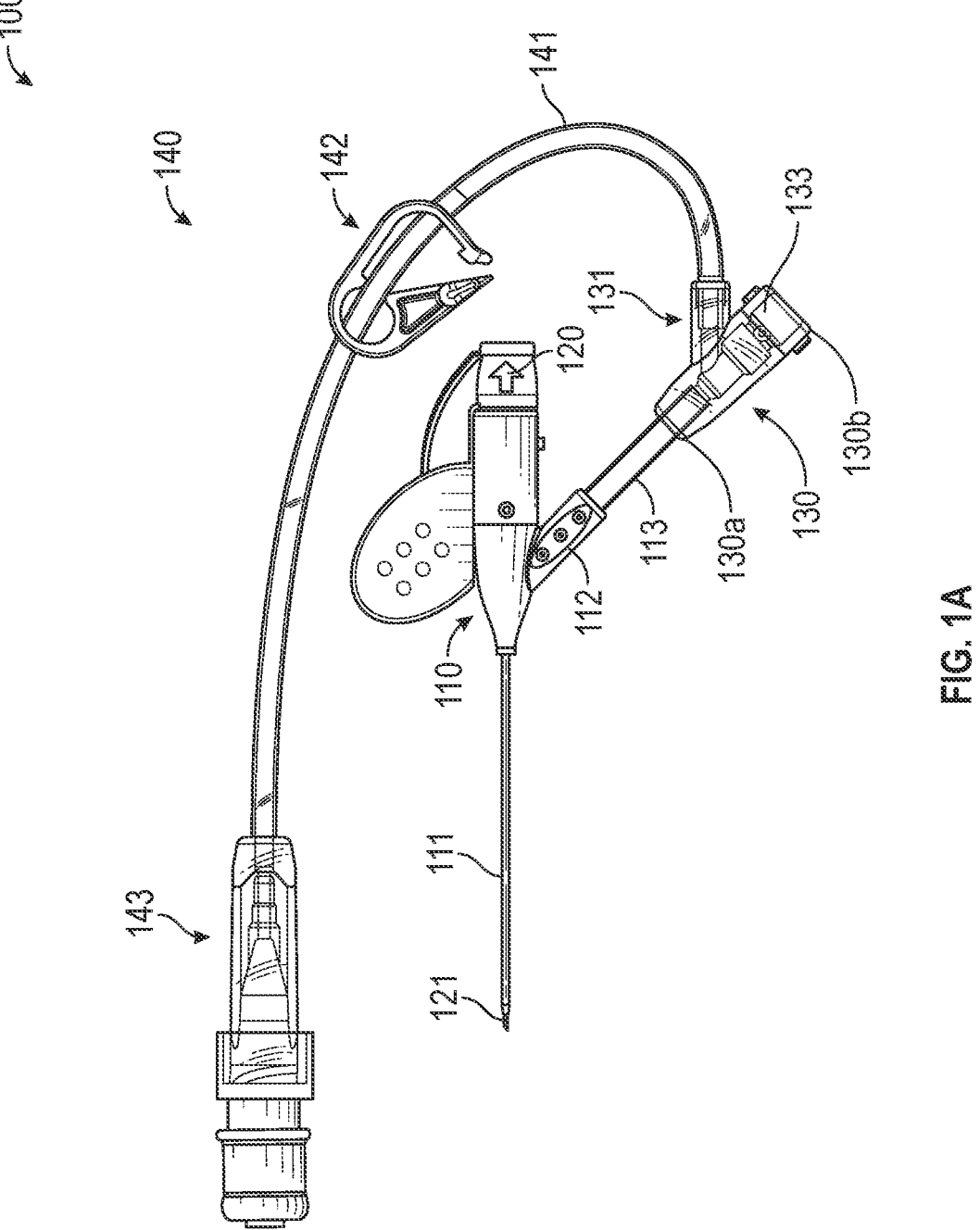
FIGS. 1A and 1B each illustrate an integrated PIVC that includes a side port in accordance with embodiments of the present disclosure.
Figure 1B:
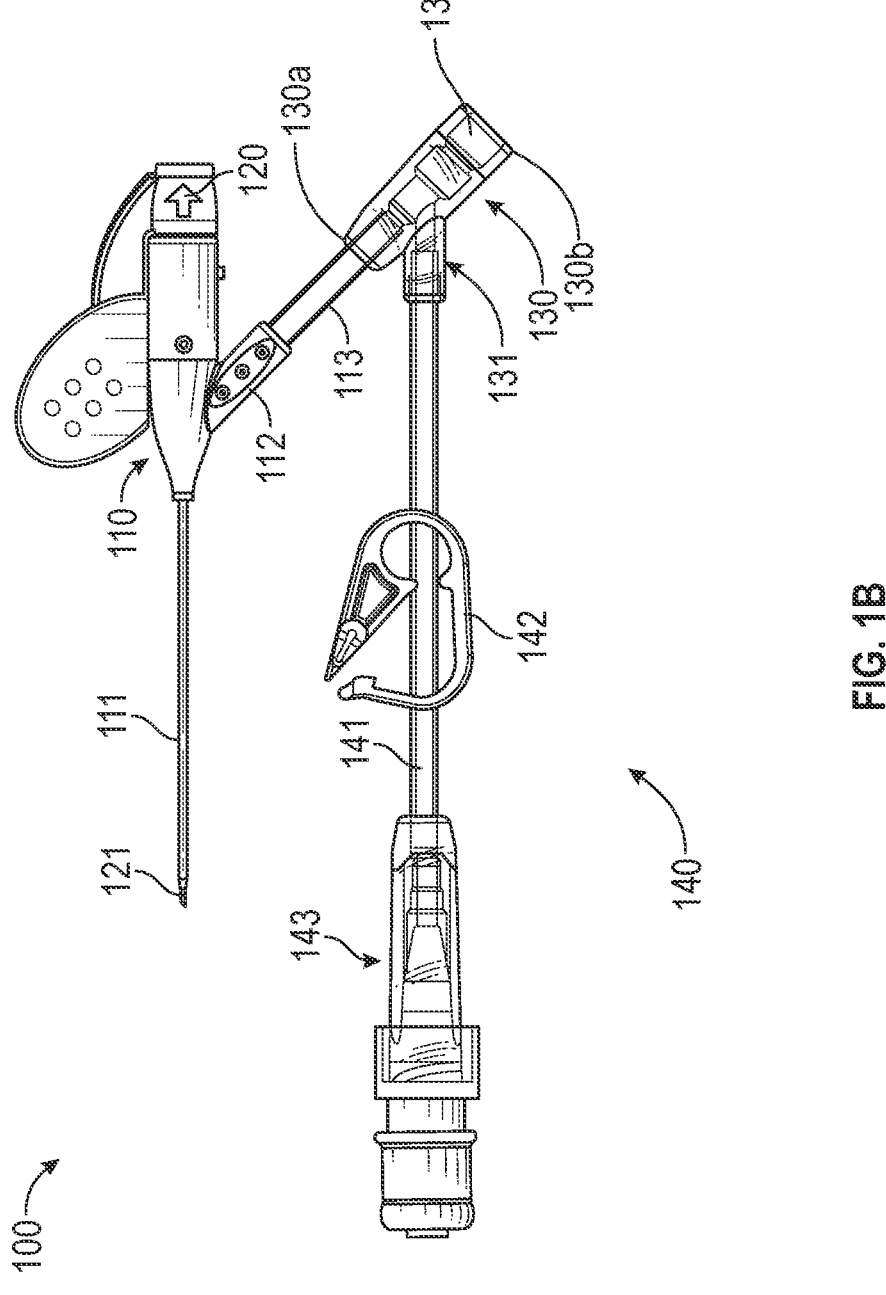

FIGS. 1A and 1B each provide an example of a PIVC 100 that is configured in accordance with embodiments of the present disclosure. PIVC 100 includes a catheter adapter 110 from which a catheter 111 distally extends and a needle assembly 120 from which a needle 121 distally extends. Prior to insertion, needle assembly 120 is coupled to catheter adapter 110 to cause needle 121 to extend distally from catheter 111. Catheter adapter 110 also includes a side inlet 112 which defines a fluid pathway into and out from catheter 111. The exact configuration and function of catheter adapter 110 and needle assembly 120 are not essential to the present disclosure and any suitable configuration and/or interaction of these components could be employed.

PIVC 100 also includes a side port 130 having a distal end 130*a* that is coupled to side inlet 112 via intermediate tubing 113, a proximal end 130*b* housing a septum 133 (or other flow control component) and a side branch 131 by which an extension set 140 is integrated with side port 130. As depicted, extension set 140 can include extension tubing 141 that extends between side branch 131 and an access port 143 and a pinch clamp 142 for occluding extension tubing 141. It is noted, however, that many different types and configurations of extension sets could be used with embodiments of the present disclosure. Of importance is that side port 130 is positioned between extension set 140 and catheter adapter 110.

Side port 130 defines two fluid pathways. One fluid pathway extends between distal end 130*a* and proximal end 130*b*. As described in detail below, this fluid pathway may be used to collect a blood sample through PIVC 100 by connecting a blood collection set/adapter to proximal end 130*b*. The other fluid pathway extends between distal end 130*a* and side branch 131 and is therefore the fluid pathway into and out from extension set 140.

In FIG. 1A, side branch 131 has a distally-directed orientation relative to the main body of side port 130. In other words, side branch 131 is oriented away from septum 133. In contrast, in FIG. 1B, side branch 131 has a proximally-directed orientation and is therefore oriented towards septum 133. This proximally-directed orientation causes fluid flowing from extension set 140 to be directed against septum 133 to thereby flush residual blood or other fluid from septum 133.

Figure 2:
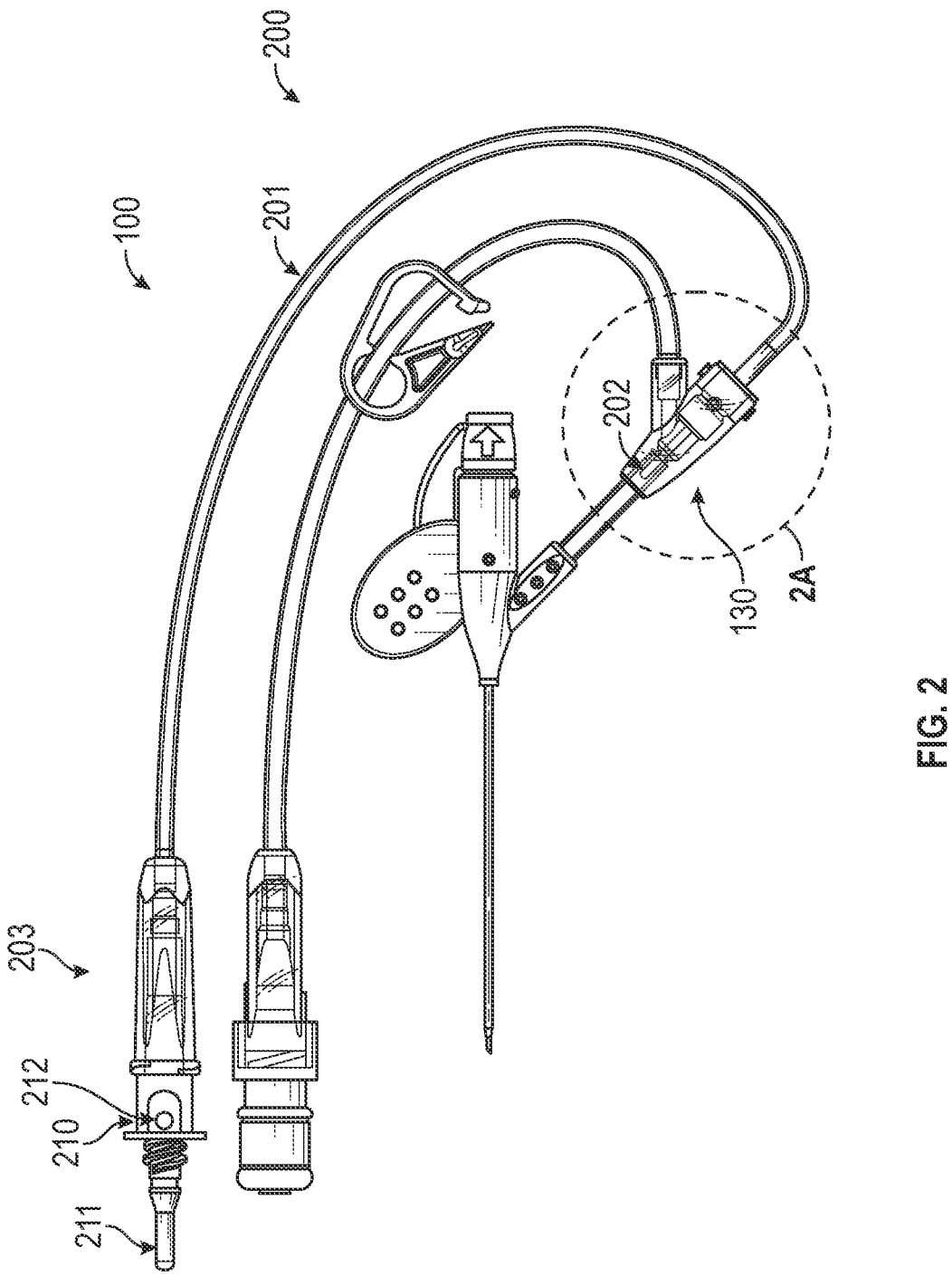
FIG. 2 illustrates an integrated PIVC that includes a side port to which a blood collection set is pre-attached.
Figure 2A:
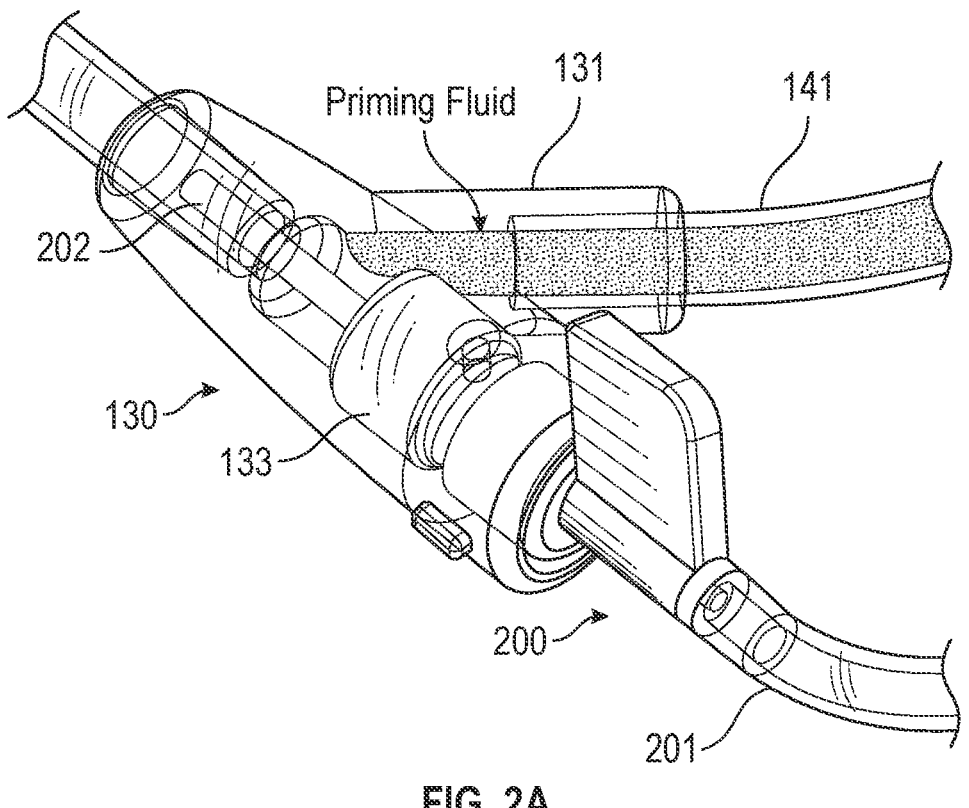
FIG. 2A provides a detailed view of the side port of the integrated PIVC shown in FIG. 2.

FIG. 2 illustrates PIVC 100 as depicted in FIG. 1A but with the addition of a pre-attached blood collection set 200. Blood collection set 200 includes tubing 201, a cannula 202 that extends from a distal end of tubing 201 and an access port 203 coupled to a proximal end of tubing 201. A blood collection adapter 210 may also be integrated into or pre-attached to access port 203. Blood collection adapter 210 includes a shielded cannula 211 and an air vent 212. As best seen in FIG. 2A, blood collection adapter 210 can be pre-attached to PIVC 100 by inserting cannula 202 into proximal end 130*b* of side port 130 and through septum 133.

In some embodiments, extension set 140 can be primed before inserting PIVC 100 into the patient's vasculature. For example, FIG. 2A represents that at least the lower end of extension tubing 141 has been filled with priming fluid. This priming fluid can be retained within extension tubing 141 by activating pinch clamp 142. Whether or not extension tubing 141 is primed, catheter 111 can be inserted into the patient's vasculature. Due to the pre-attachment of blood collection set 200 and air vent 212, blood will commence flowing through side port 130 and into tubing 201 until it reaches blood collection adapter 210. At that point, a blood collection tube (e.g. a vacuum tube) can be connected to blood collection adapter 210 to collect a blood sample. Once the blood sample is collected, blood collection set 200 can be removed from side port 130 (e.g., by withdrawing cannula 202 from septum 133). Extension set 140 may then be used to inject a fluid into the patient's vasculature via side port 130. As can be seen, side port 130, and particularly the pre-attachment of blood collection set 200 to side port 130, enables a blood sample to be collected initially at the time of catheter insertion through a different fluid pathway from the fluid pathway that will be used to subsequently inject a fluid. Notably, this enables extension set 140 to be pre-primed while also enabling the collection of the blood sample while extension set 140 remains primed.

Figure 3:
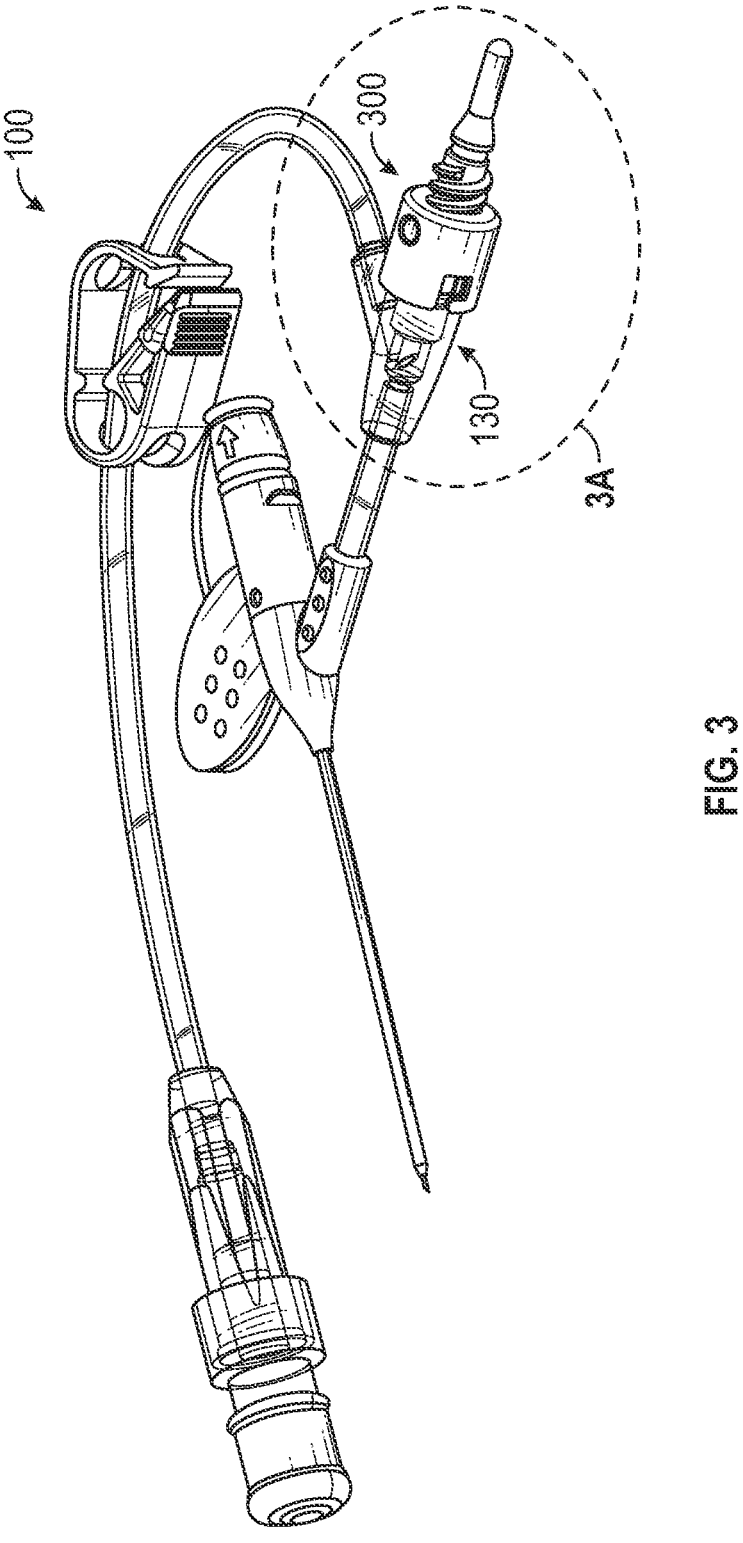
FIG. 3 illustrates an integrated PIVC that includes a side port to which a blood collection adapter is pre-attached.

In some cases, the use of blood collection set 200 may still be undesirable. For example, given the length of tubing 201, it may require a substantial amount of time for blood to flow up to blood collection adapter 210. Similarly, when a patient's blood pressure is low, there may be insufficient blood flow through tubing 201 even when a vacuum tube is used for the blood collection. To minimize such issues, a blood collection adapter 300 may be coupled directly to side port 130 as shown in FIG. 3.

Figure 3A:
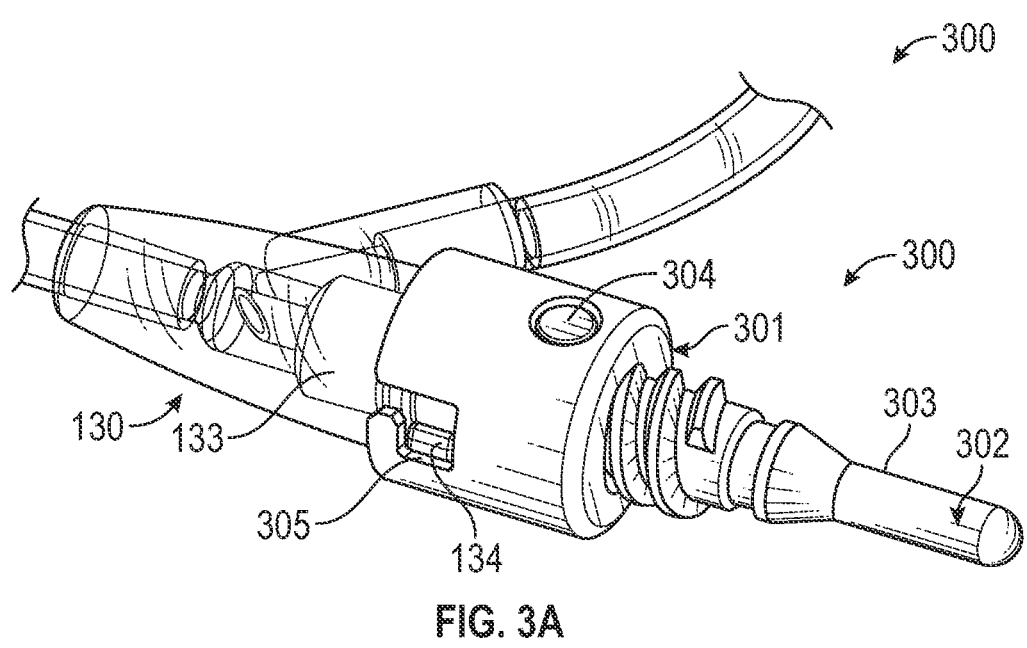
FIG. 3A provides a detailed view of the side port and pre-attached blood collection adapter of the integrated PIVC shown in FIG. 3.
Figure 3B:
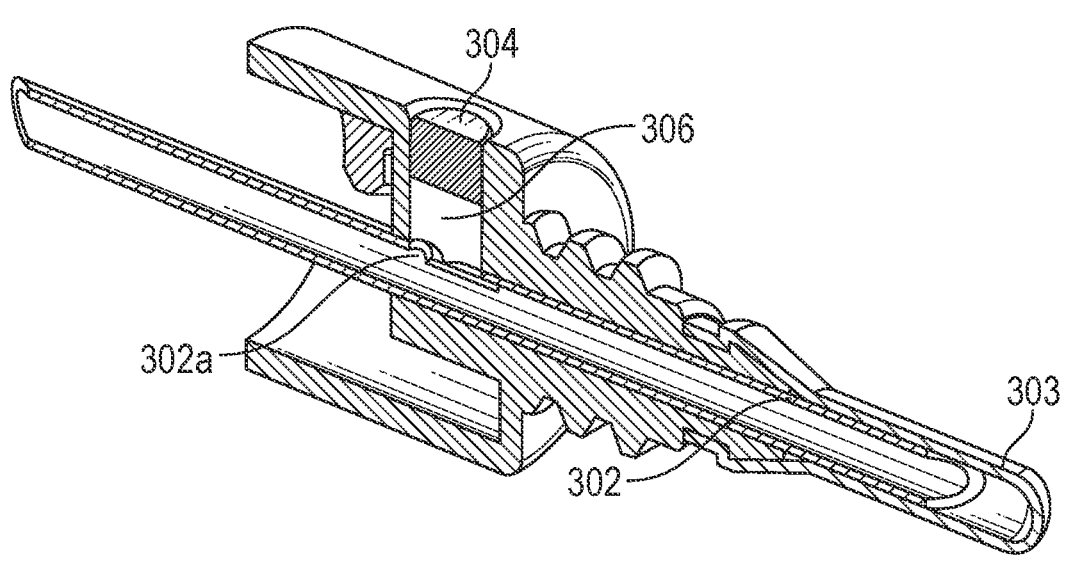
FIG. 3B provides a cross-sectional view of the blood collection adapter of FIG. 3.

As best shown in FIGS. 3A and 3B, blood collection adapter 300 includes a housing 301 that is configured to attach to proximal end 130*b* of side port 130. Blood collection adapter 300 also includes a cannula 302 that extends through housing 301. A distal end of cannula 302 may extend beyond housing 301 such that cannula 302 will extend through septum 133 when housing 301 is attached to side port 130. A proximal end of cannula 302 also extends beyond housing 301 and is covered by a sheath 303.

Housing 301 may form a slot 305 that can receive a protrusion 134 formed on the exterior of side port 130 to thereby lock blood collection adapter 300 to side port 130. For example, in the depicted embodiment, a portion of housing 301 is positioned distal to slot 305 such that, when protrusion 134 is positioned in slot 305, blood collection adapter 300 cannot be separated from side port 130 without first rotating blood collection adapter 300 relative to side port 130. Housing 301 may include threads or any other suitable structure for receiving/securing a blood collection tube.

An air vent 304 is positioned within a channel 306 in housing 301. Channel 306 can align with an opening 302*a* in cannula 302 to thereby allow air within cannula 302 to be vented through air vent 304. Accordingly, when catheter 111 is inserted into the patient's vasculature, air will be vented from side port 130 to thereby allow blood to flow through side port 130 and up to the proximal end of cannula 302. At that point, a blood collection tube can be connected to blood collection adapter 300 to collect a blood sample. In particular, the connection of the blood collection tube can cause cannula 302 to pierce sheath 303 thereby opening a fluid pathway into the blood collection tube. In the same manner described above, extension set 140 could be pre-primed before inserting catheter 111 into the patient's vasculature and could remain primed while the blood sample is collected via blood collection adapter 300.

Figure 4:
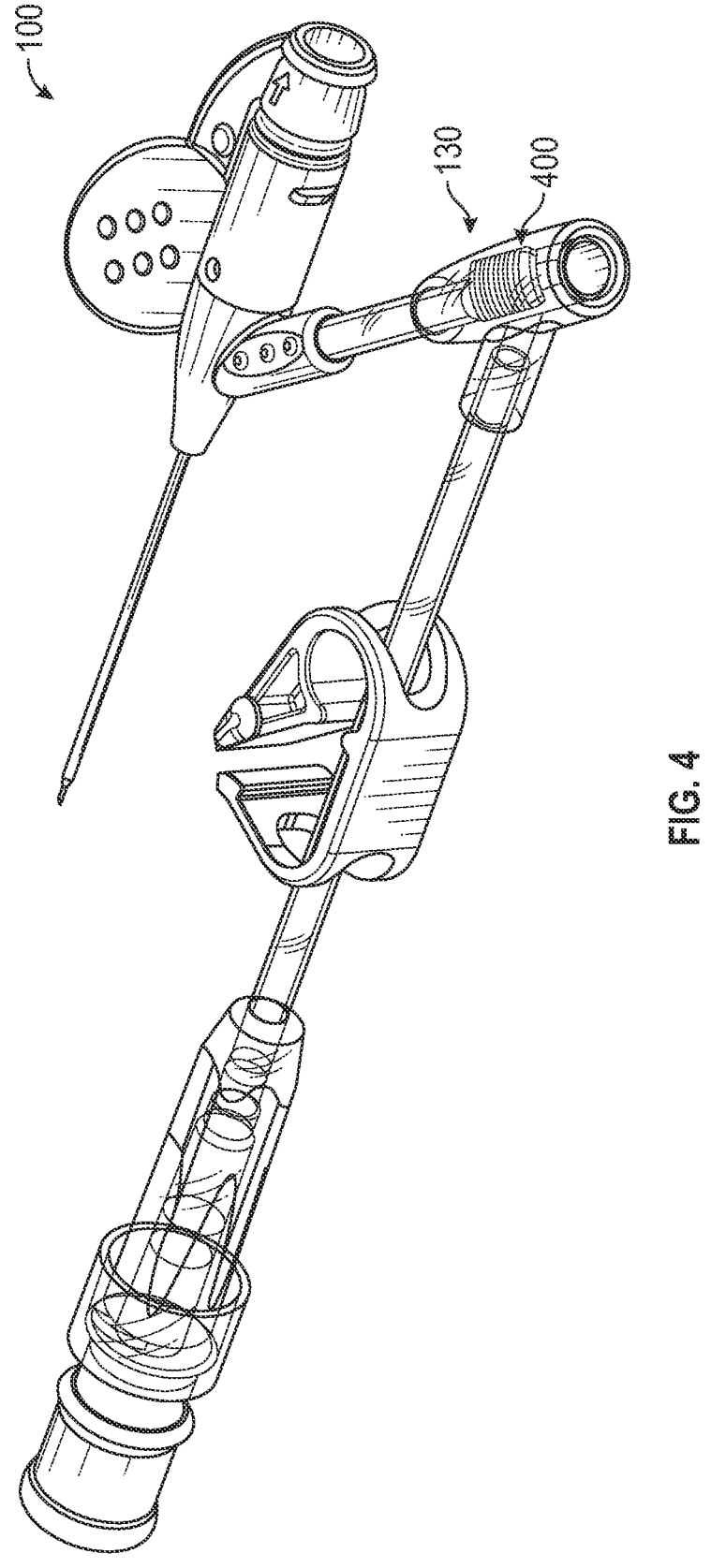
FIG. 4 illustrates an integrated PIVC that includes a side port having an active septum valve.

FIG. 4 illustrates PIVC 100 as depicted in FIG. 1B except that side port 130 includes an active septum valve 400. As best shown in FIGS. 4A-4D, active septum valve 400 includes an actuating member 410 and a septum 420. Actuating member 410 includes a sliding tab 411 and a septum housing 412 that are interconnected by a connecting portion 413. Septum 420 includes a channel 421 within which septum housing 412 is positioned to thereby secure actuating member 410 to septum 420. As a result, when actuating member 410 is slid proximally or distally, septum 420 will likewise slide proximally or distally respectively. Side port 130 includes a channel 135 within which connecting portion 413 may travel to enable this sliding of active septum valve 400 from a closed (distal) position to an open (proximal) position and vice versa.

Figure 4A:
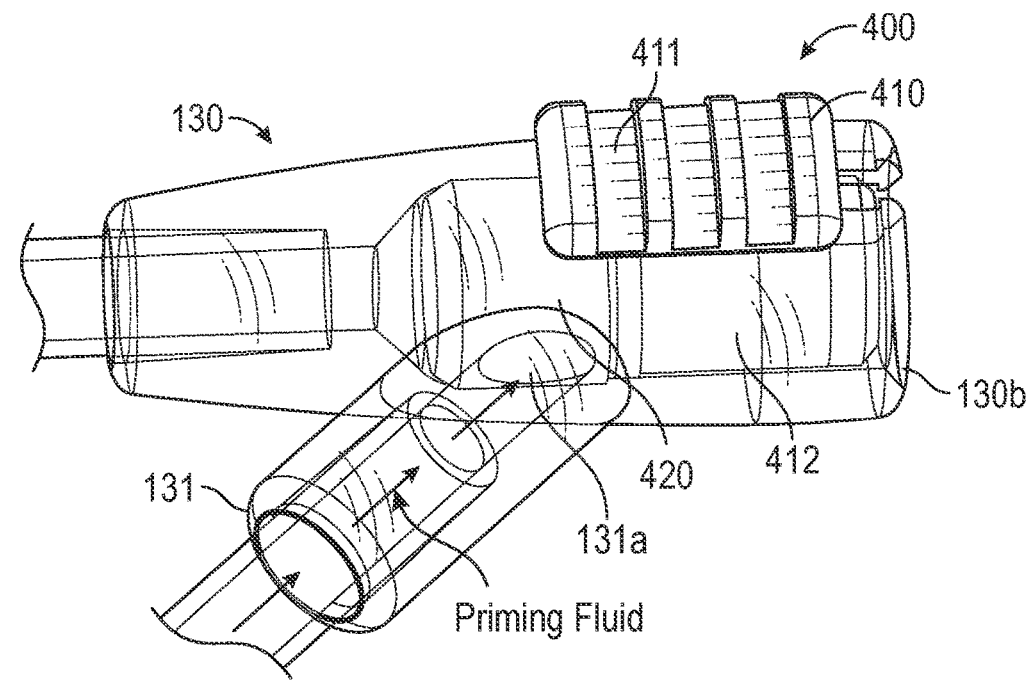
FIGS. 4A and 4B illustrate the active septum valve in a closed position and an open position respectively.
Figure 4B:
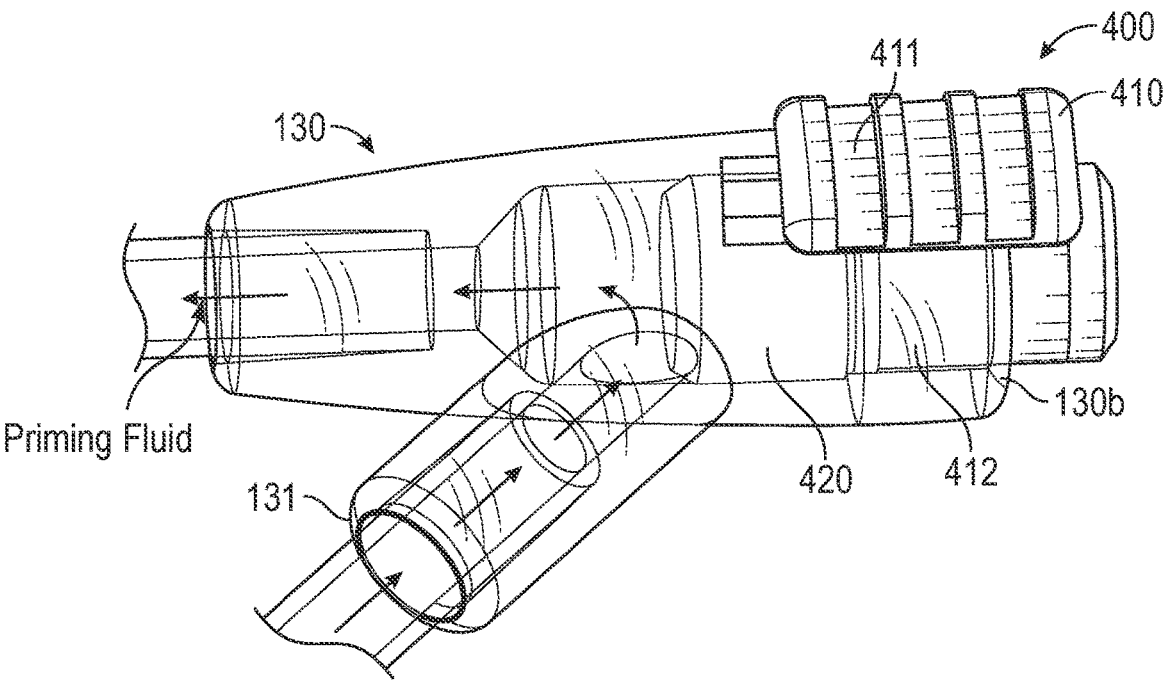
Figure 4C:
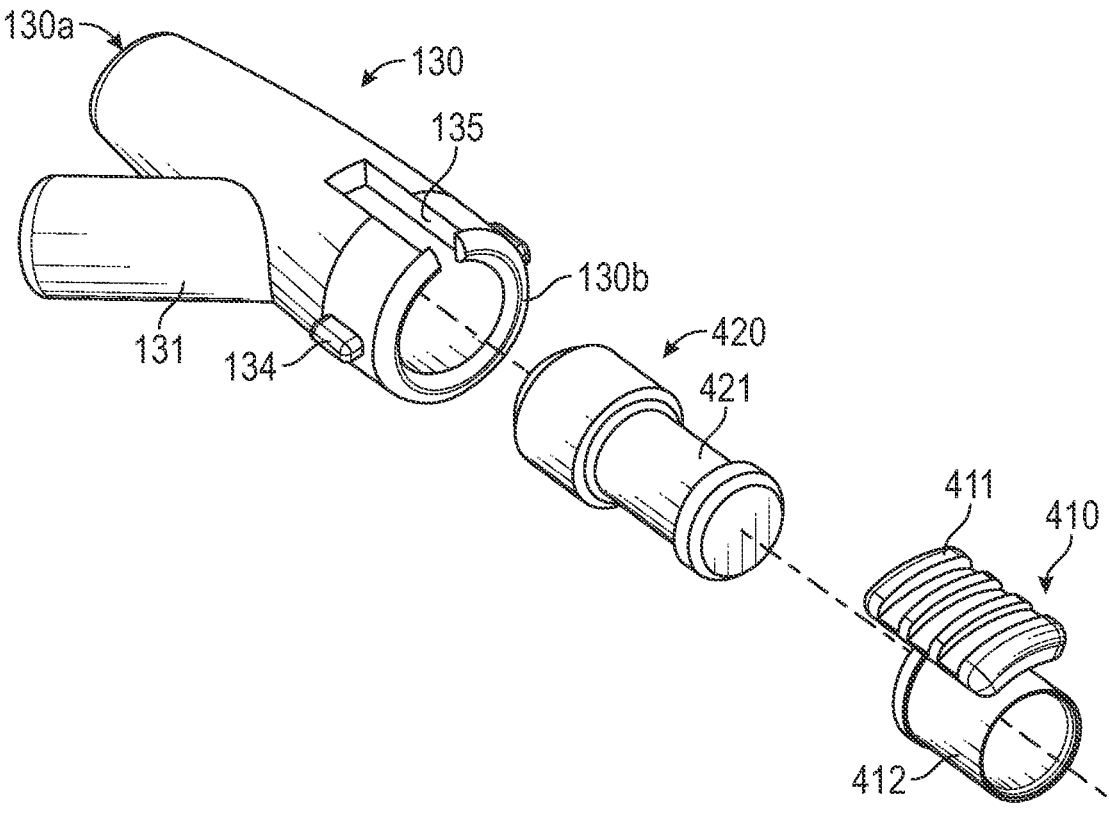
FIG. 4C provides an exploded view of the side port and active septum valve.
Figure 4D:
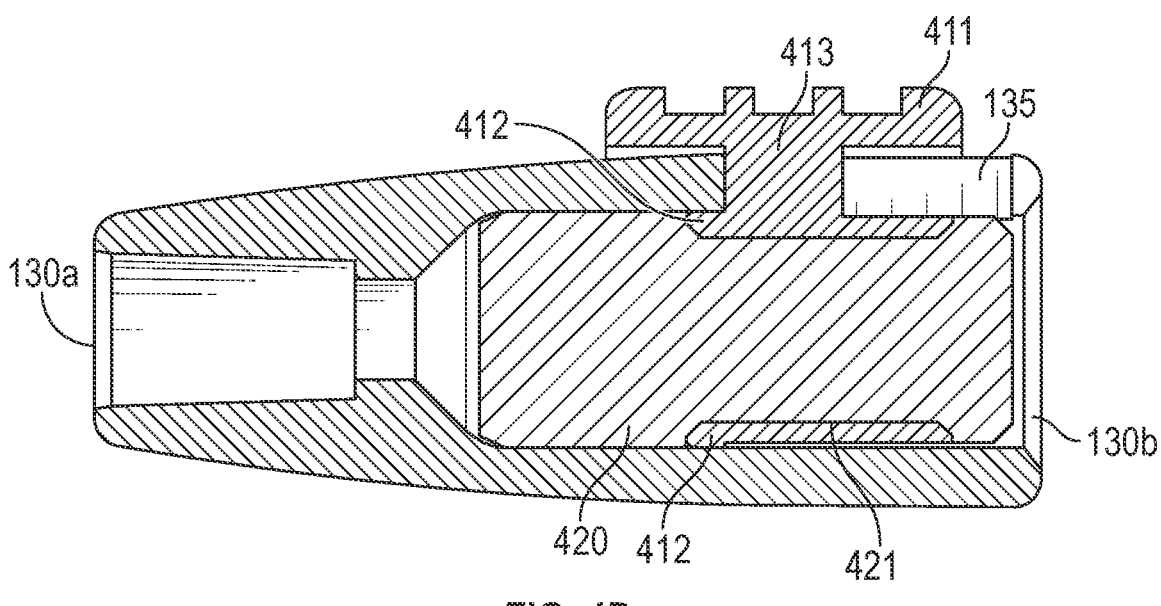
FIG. 4D provides a cross-sectional view of the side port and active septum valve.

FIGS. 4A and 4B illustrate side port 130 when active septum valve 400 is in the closed and open positions respectively. Active septum valve 400 can initially be in the closed position prior to insertion of catheter 111 into the patient's vasculature. When active septum valve 400 is in the closed position, septum 420 will cover the opening of side branch 131. In other words, septum 420 will block the fluid pathway into and out from extension set 140. Accordingly, priming fluid that may be injected into extension set 140 will be prevented from flowing into side port 130 beyond side branch 131. With active septum valve 400 in this closed position, PIVC 100 can be used to collect a blood sample in any of the ways describe above such as is represented in FIGS. 4E (blood collection adapter 300) and 4F (blood collection set 200).

After collecting a blood sample, a proximal force can be applied to sliding tab 411 to cause active septum valve 400 to move into the open position shown in FIG. 4B. When active septum valve 400 is in the open position, septum 420 will no longer cover the opening of side branch 131 thereby opening the fluid pathway into and out from extension set 140. Fluid, including any priming fluid that may have been pre-injected into extension set 140, can then be injected from extension set 140 and into side port 130. This fluid can flush any residual blood in side port 130 into the patient's vasculature. Also, given the proximal orientation of side branch 131 in the depicted embodiment, this fluid will be directed against septum 420 to thereby flush any blood that may be trapped between septum 420 and the sidewall of side port 130.

Figure 4E:
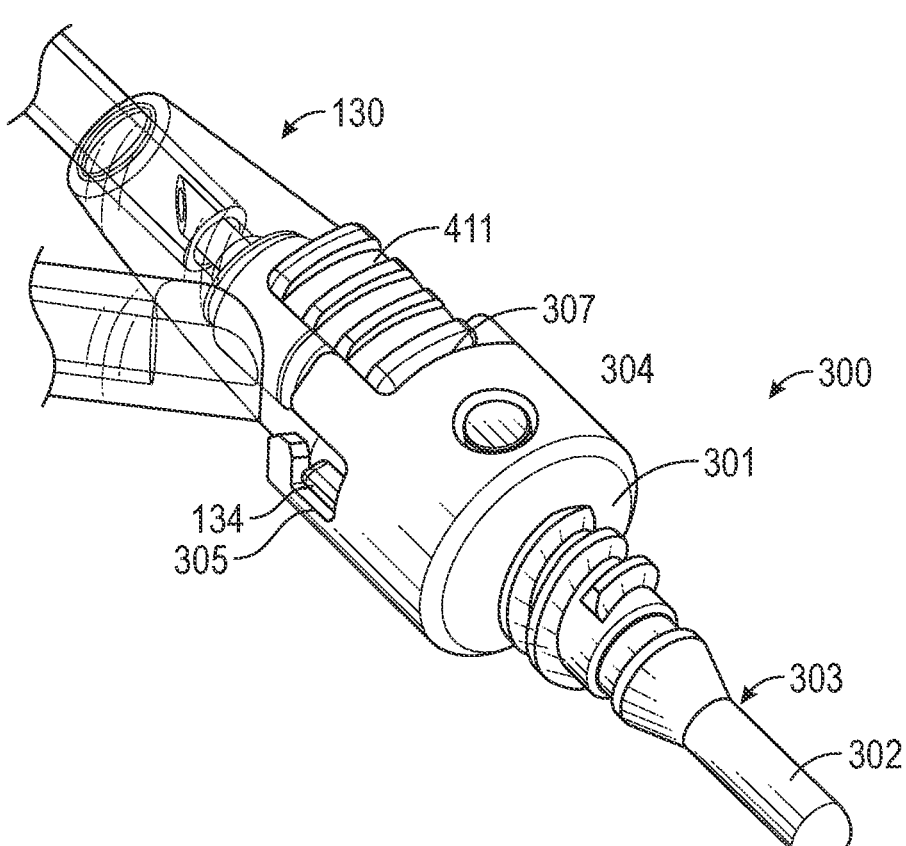
FIG. 4E illustrates how a blood collection adapter can be pre-attached to the side port having the active septum valve.
Figure 4F:
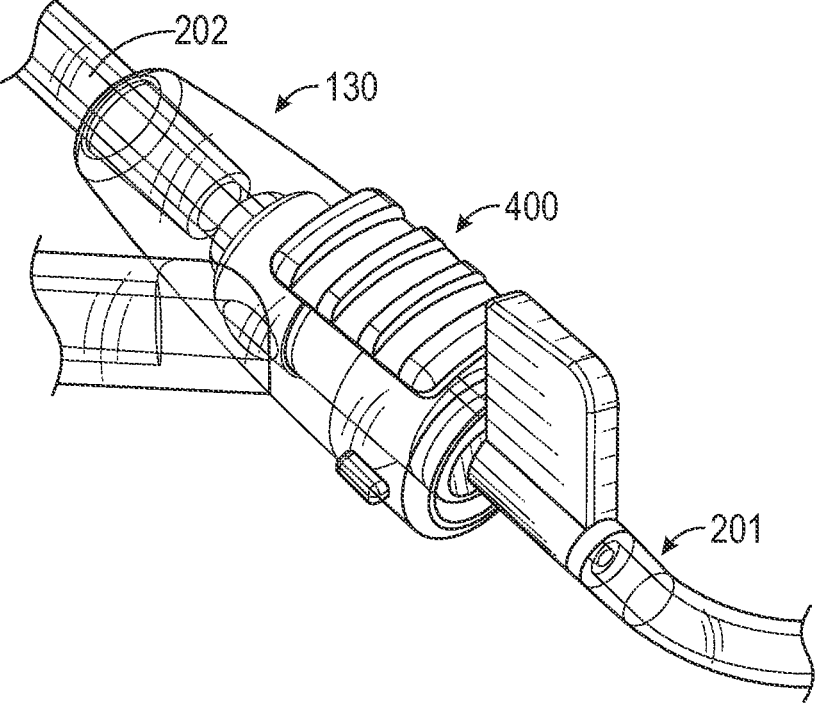
FIG. 4F illustrates how a blood collection set can be pre-attached to the side port having the active septum valve.

FIG. 4E illustrates a variation of blood collection adapter 300 that may be employed when blood collection adapter 300 is intended to be connected to side port 130 when side port 130 includes active septum valve 400. Blood collection adapter 300 as shown in FIG. 4E is the same as described above with the addition of a distally-facing slot 307 against which sliding tab 411 abuts when protrusion 134 is inserted into slot 305. Slot 307 functions to prevent active septum valve 400 from being transitioned into the open position until after blood collection adapter 300 is removed from side port 130. More particularly, to position protrusion 134 within slot 305, sliding tab 411 will need to be in its distal-most position (or at least in a position that causes septum 420 to cover the opening of side branch 131). Then, with protrusion 134 positioned in slot 305, slot 307 will prevent sliding tab 411 from sliding proximally. In this way, the fluid pathway of extension set 140 can remain isolated until after a blood sample is collected through side port 130 (or at least until blood collection adapter 300 is removed).

Figure 5:
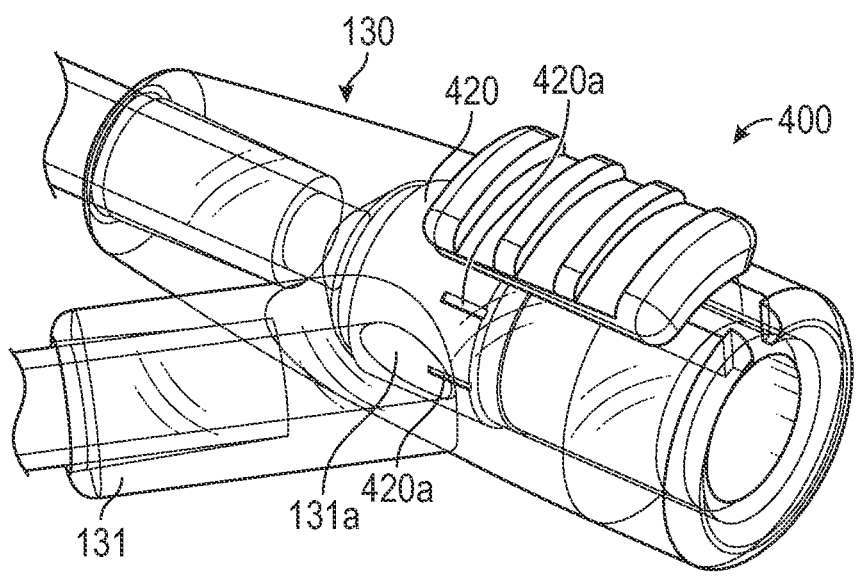
FIG. 5 illustrates a side port of an integrated PIVC where the side port includes an active septum valve with venting channels.
Figure 5A:
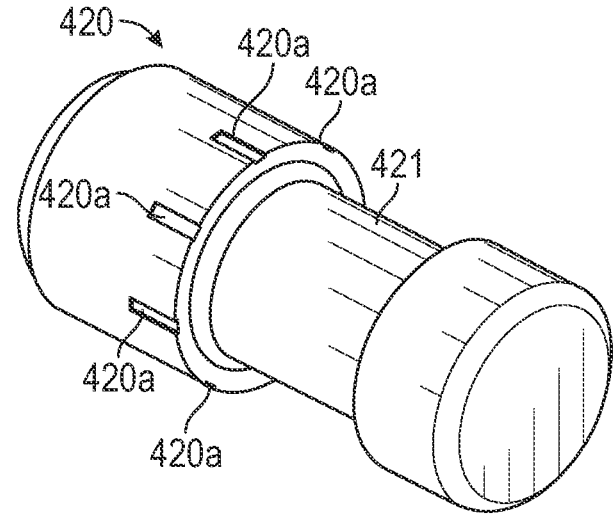
FIG. 5A illustrates the active septum valve of FIG. 5 in isolation.
Figure 5B:
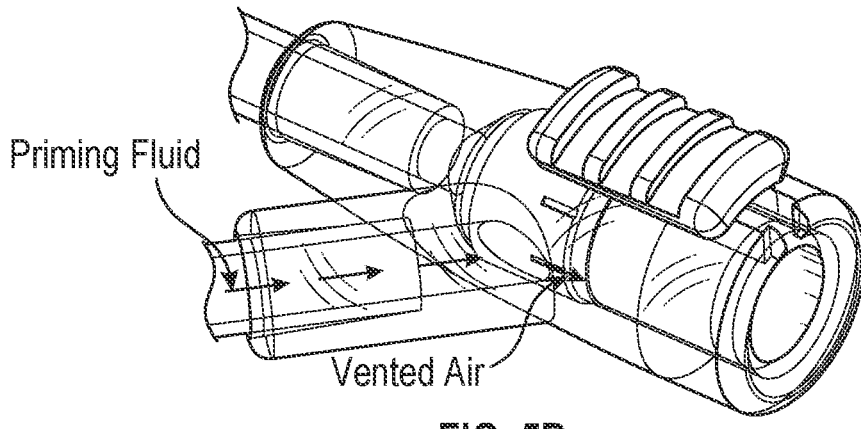
FIG. 5B represents how the venting channels allow air to be vented from extension tubing of the integrated PIVC while retaining priming fluid within the extension tubing.

FIGS. 5, 5A and 5B illustrate a variation of active septum valve 400 that may be employed on some embodiments of the present disclosure. As best shown in FIG. 5A, a number of venting channels 420a can be formed around the portion of septum 420 that is distal to channel 421. Notably, this distal portion of septum 420 in which venting channels 420a are formed covers an opening 131a of side branch 131. Venting channels 420a can extend to channel 421 so that air can pass along septum housing 412 and out from side port 130 (e.g., via channel 135 and/or proximal end 130b. Venting channels 420a can be configured (e.g., sized) to enable the passage of air but not fluids. Accordingly, in cases where extension set 140 may be pre-primed, venting channels 420a will allow air to vent from within extension set 140 while blocking the priming fluid from flowing out of extension set 140. In this way, venting channels 420a facilitate the priming of extension set 140 while active septum valve 400 is in the closed position.

Figure 6:
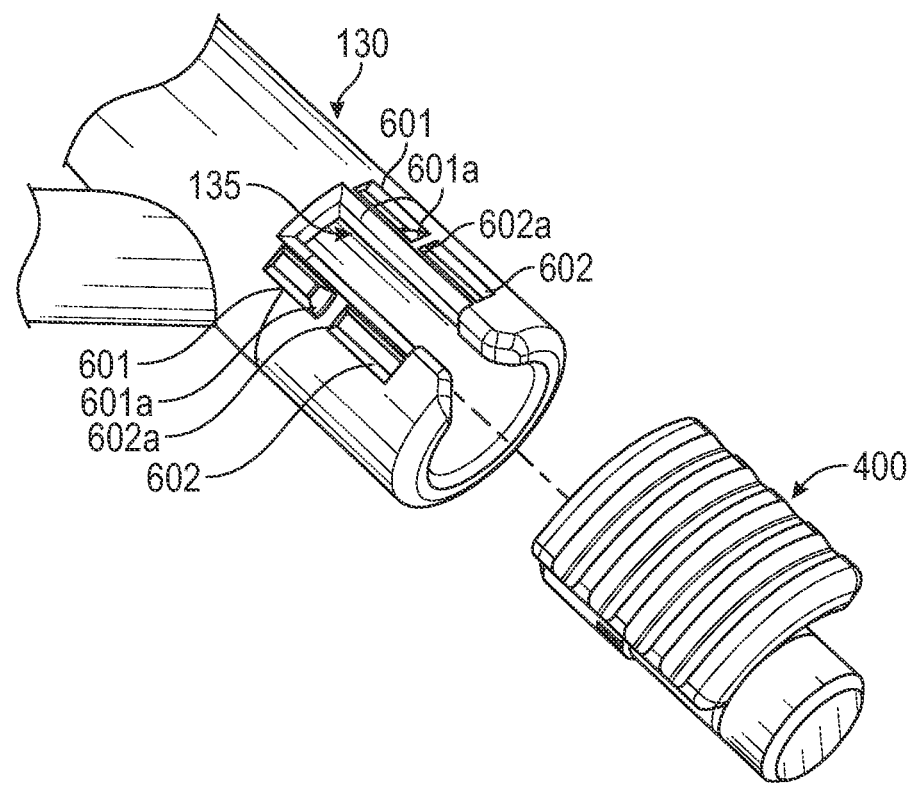
FIG. 6 illustrates a side port of an integrated PIVC where the side port includes an active septum valve that is configured for one time activation.
Figure 6A:
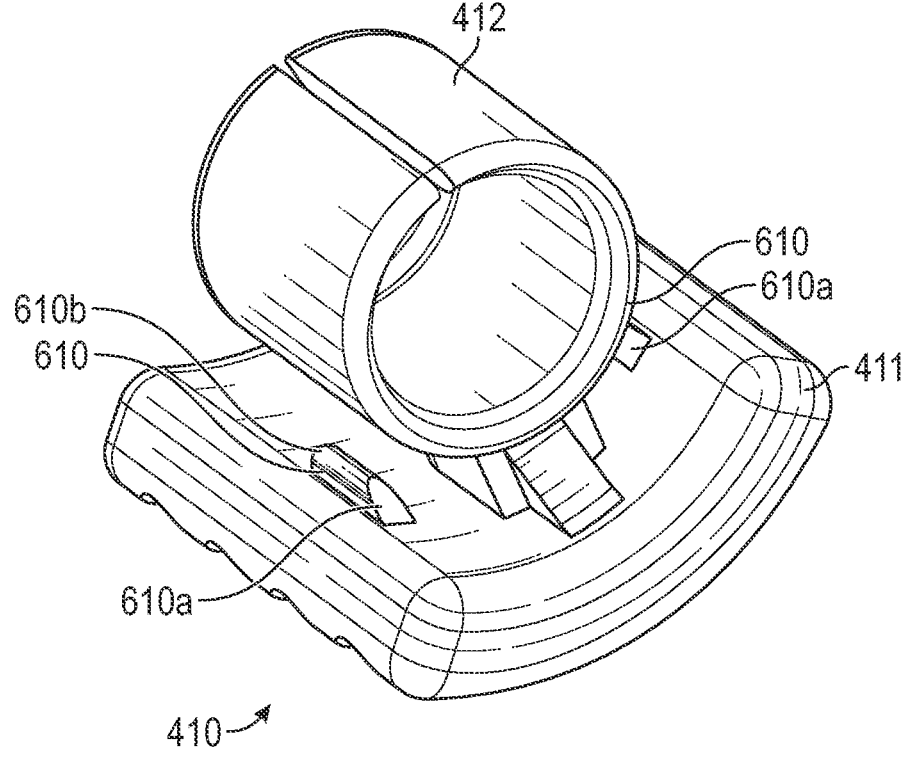
FIG. 6A illustrates the active septum valve of FIG. 6.

FIGS. 6 and 6A-6C illustrate another variation of active septum valve 400 that may be employed on some embodiments of the present disclosure to allow active septum valve 400 to be activated (or moved from the closed position to the open position) a single time. As shown in FIG. 6A, tabs 610 may be formed on the underside of sliding tab 411 on opposite sides of connecting portion 413. Each tab 610 includes a ramped proximal end 610a and a distal end 610b. As shown in FIG. 6, side port 130 can include corresponding distal slots 601 and proximal slots 602 on opposite sides of channel 135. Each distal slot 601 includes a ramped proximal end 601a.

Figure 6B:
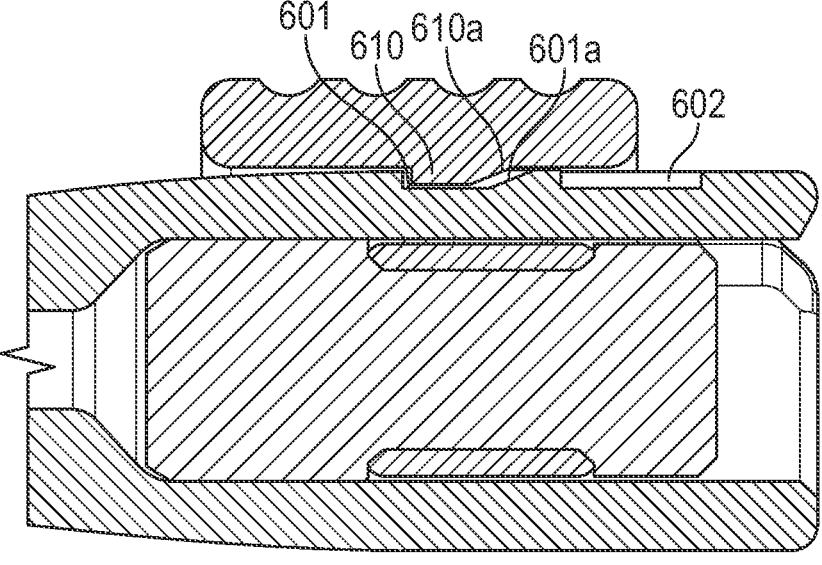
FIGS. 6B and 6C provide cross-sectional views of the side port of FIG. 6 when the active septum valve is in a closed position and an open position respectively.
Figure 6C:
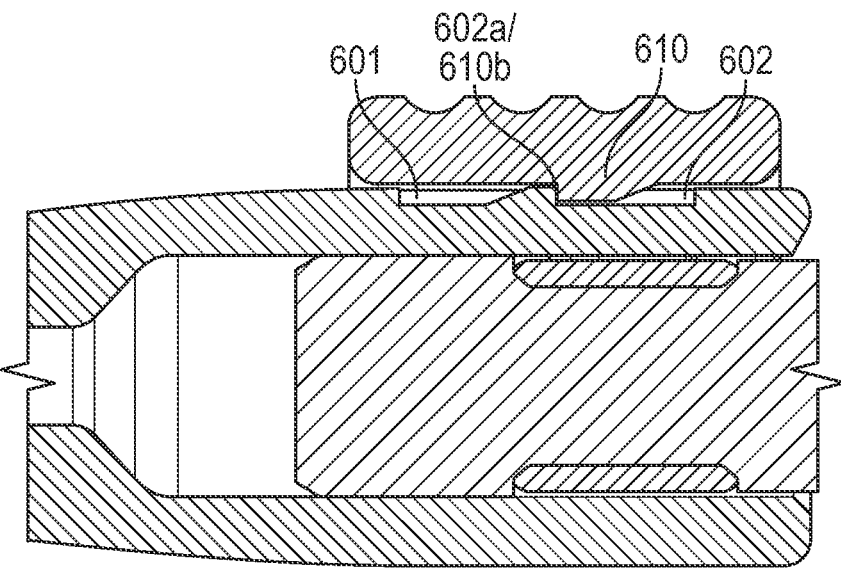

FIG. 6B illustrates side port 130 when active septum valve 400 is in the closed position. In this closed position, tabs 610 will insert into distal slots 601 with ramped proximal end 610a of tab 610 substantially aligning with ramped proximal end 601a of distal slot 601. Because these ends are correspondingly ramped, when a proximal force is applied to sliding tab 411, ramped proximal end 610a will slide upwardly along and relative to proximal end 601a of distal slot 601 such that each tab 610 will escape the corresponding distal slot 601. Further proximal movement will then cause each tab 610 to drop into the corresponding proximal slot 602 as represented in FIG. 6C. Each proximal slot 602 includes a distal end 602a that is not ramped relative to distal end 610b of the corresponding tab 610. Accordingly, the interaction between these distal ends will block distal movement of each tab 610 thereby preventing active septum valve 400 from being returned to the closed position. Therefore, in these embodiments, once active septum valve 400 has been slid into the open position, the fluid pathway through extension set 140 will remain open.

Figure 7:
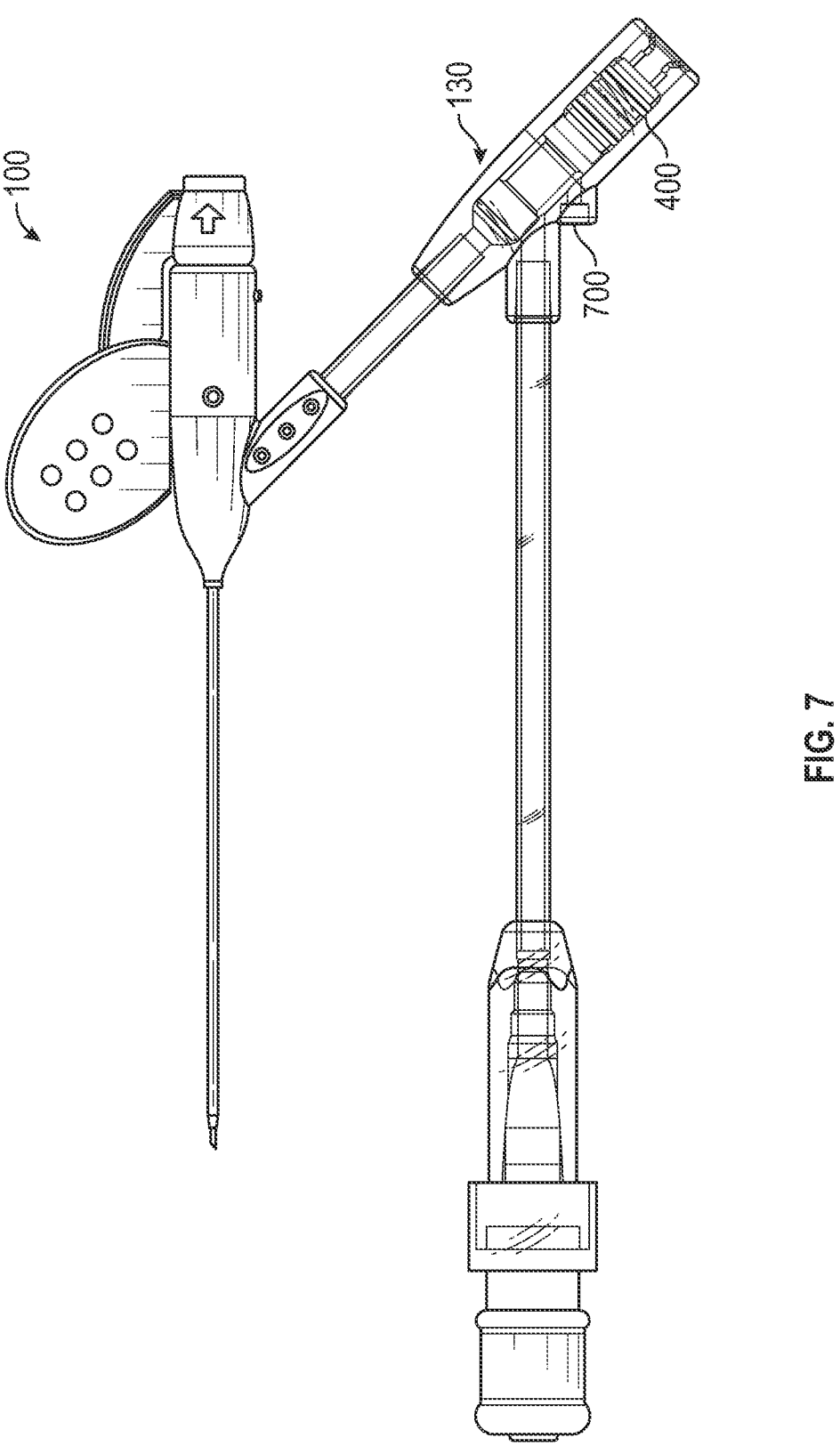
FIG. 7 illustrates an integrated PIVC that includes a side port having an air venting membrane and an active septum valve.
Figure 7A:
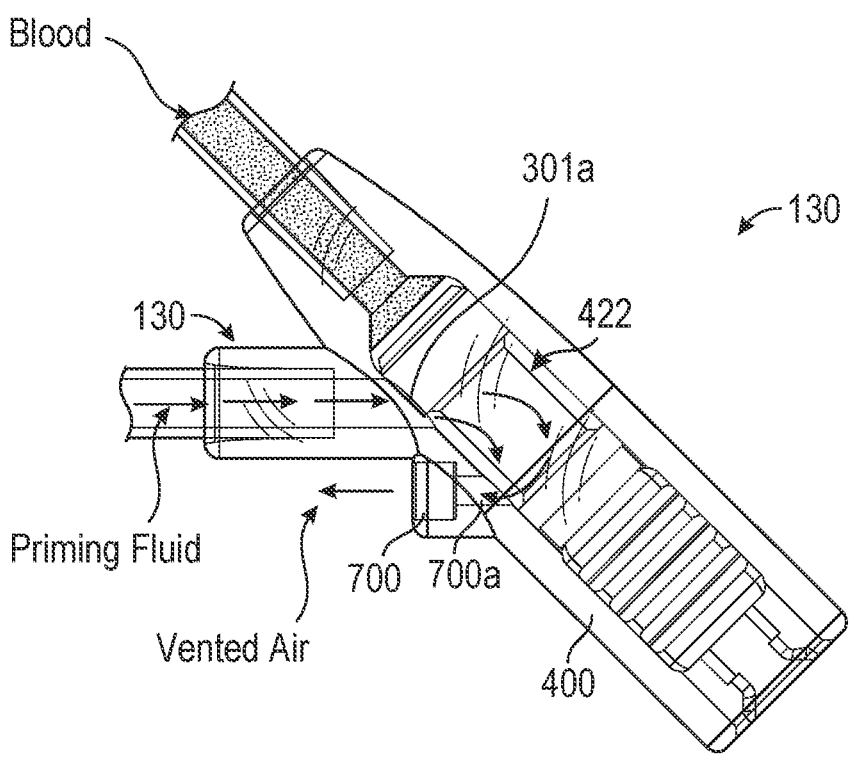
FIGS. 7A and 7B represent fluid and air flow through the side port of FIG. 7 when the active septum valve is in a closed position and an open position respectively.
Figure 7B:
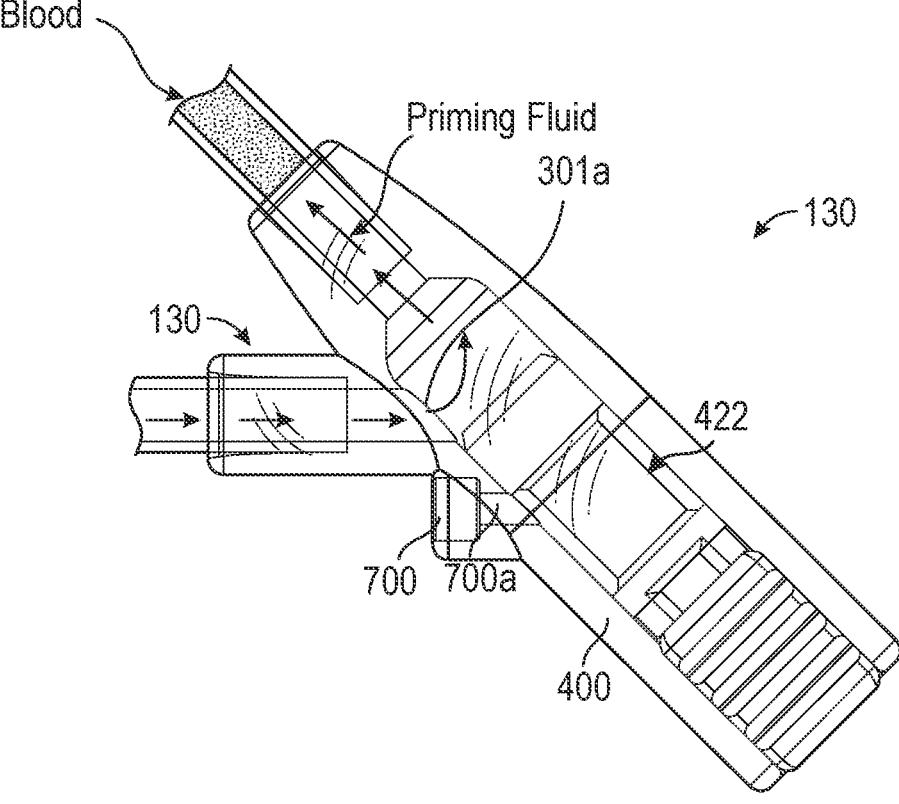

FIGS. 7 and 7A-7B illustrate a variation of side part 130 that may be employed on PIVC 100 in some embodiments of the present disclosure. In these embodiments, a venting membrane 700 is integrated into a venting channel 700a in side port 130. Venting channel 700a is positioned proximal to side branch 131. Additionally, septum 420 of active septum valve 400 includes a venting channel 422 that is positioned distal to channel 421. As best shown in FIG. 7A, venting channel 422 can be configured to extend partially overtop opening 131a of side branch 131 when active septum valve 400 is in the closed position to thereby form an air pathway from extension set 140 into venting channel 422. Venting channel 422 can also be configured to extend at least partially overtop venting channel 700a to thereby extend the air pathway to venting membrane 700. In this way, air can be vented from extension set 140 when active septum valve 400 is in the closed position to thereby facilitate priming extension set 140. After a blood sample is collected, active septum valve 400 can be slid proximally so that septum 420 no longer blocks opening 131a. Extension set 140 can then be used to inject a fluid including to flush residual blood as shown in FIG. 7B.

In view of the foregoing, it can be seen that a PIVC configured in accordance with embodiments of the present disclosure can facilitate the collection of a blood sample at the time of catheter insertion and even before withdrawing the needle from the patient's vasculature. This collection of the blood sample can be accomplished through a different fluid pathway from the fluid pathway used to subsequently inject fluids into the patient's vasculature. Accordingly, blood will not come in contact with the access port of the extension set used for such injections thereby reducing the risk of BSI. Various configurations of the PIVC even allow this blood collection process to be performed while the extension set is primed without the risk of diluting the blood sample with priming solution.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. An integrated intravenous (IV) catheter comprising:
   a catheter adapter having a catheter that is configured to be inserted into a patient's vasculature;
   a side port having a distal end by which the side port is connected to the catheter adapter, a proximal end, and a side branch, wherein the proximal end of the side port provides a first fluid pathway for drawing blood from the patient's vasculature and the side branch of the side port provides a second fluid pathway for injecting fluids into the patient's vasculature, wherein the side port further comprises an active septum valve, wherein the active septum valve comprises an actuating member and a septum, wherein the actuating member comprises a sliding tab positioned external to the side port such that the sliding tab is accessible to a clinician for manual actuation, a septum housing positioned internal to the side port and a connecting portion that connects the sliding tab to the septum housing, wherein the septum is secured to the septum housing, wherein the active septum valve is positioned at the proximal end of the side port and includes a closed position in which the septum covers the side branch to thereby close the second fluid pathway and an open position in which the septum does not cover the side branch to thereby open the second fluid pathway, and wherein the sliding tab is configured to slide proximally relative to the side port in response to the clinician's manual actuation to thereby move the active septum valve from the closed position to the open position and to slide distally relative to the side port in response to the clinician's manual actuation to thereby move the active septum valve from the open position to the closed position; and
   an extension set that is connected to the side port via the side branch.

2. The integrated IV catheter of claim 1, further comprising:
   a blood collection set that inserts through the active septum valve, the blood collection set being configured to vent air from the first fluid pathway.

3. The integrated IV catheter of claim 1, further comprising:
   a blood collection adapter that is coupled to the proximal end of the side port and that extends through the active septum valve, the blood collection adapter being configured to vent air from the first fluid pathway.

4. The integrated IV catheter of claim 1, wherein the active septum valve includes one or more venting channels that vent air from the second fluid pathway when the active septum valve is in the closed position.

5. The integrated IV catheter of claim 1, wherein the active septum valve includes an actuating member having one or more tabs that interface with the side port to prevent the active septum valve from being moved from the open position to the closed position.

6. The integrated IV catheter of claim 5, wherein, for each of the one or more tabs, the side port includes a distal slot in which the tab is inserted when the active septum valve is in the closed position and a proximal slot in which the tab is inserted when the active septum valve is in the open position, the distal slot being configured to allow the tab to slide proximally out of the distal slot, the proximal slot being configured to prevent the tab from sliding distally out of the proximal slot.

7. The integrated IV catheter of claim 1, wherein the side port further includes a venting membrane that is positioned between the side branch and the proximal end of the side port, the active septum valve being configured to allow air contained in the extension set to escape through the venting membrane with the active septum valve is in the closed position.

8. The integrated IV catheter of claim 1, further comprising:
   a blood collection adapter that is connected to the proximal end of the side port.

9. The integrated IV catheter of claim 8, wherein the blood collection adapter prevents the active septum valve from moving to the open position.

10. The integrated IV catheter of claim 1, wherein the integrated IV catheter is a peripheral integrated IV catheter.

11. An integrated peripheral IV catheter (PIVC) comprising:
   a catheter adapter having a catheter that is configured to be inserted into a patient's vasculature;
   a side port having a distal end by which the side port is connected to the catheter adapter, a proximal end, and a side branch, wherein the proximal end of the side port provides a first fluid pathway for drawing blood from the patient's vasculature and the side branch of the side port provides a second fluid pathway for injecting fluids into the patient's vasculature, wherein the side port further comprises an active septum valve, wherein the active septum valve comprises an actuating member and a septum, wherein the actuating member comprises a sliding tab positioned external to the side port, a septum housing positioned internal to the side port and a connecting portion that connects the sliding tab to the septum housing, wherein the septum is secured to the septum housing, wherein the active septum valve is positioned at the proximal end of the side port and includes a closed position in which the septum covers the side branch to thereby close the second fluid pathway and an open position in which the septum does not cover the side branch to thereby open the second fluid pathway, and wherein the sliding tab is configured to slide proximally relative to the side port to move the active septum valve from the closed position to the open position and to slide distally relative to the side port to move the active septum valve from the open position to the closed position;
   an extension set that is connected to the side port via the side branch to thereby form an extension of the second fluid pathway when the active septum valve is in the open position; and
   a blood collection adapter that is connected to the proximal end of the side port, the blood collection adapter comprising a cannula that extends through the septum when the active septum valve is in the closed position to thereby form an extension of the first fluid pathway, wherein the blood collection adapter interfaces with the sliding tab to prevent the active septum valve from moving from the closed position to the open position until the blood collection adapter is removed from the proximal end of the side port.

12. The integrated PIVC of claim 11, wherein the septum vents air from the extension set when the active septum valve is in the closed position.

13. The integrated PIVC of claim 11, wherein the proximal end of the side port includes a protrusion and the blood collection adapter includes a slot that receives the protrusion to connect the blood collection adapter to the proximal end of the side port, and wherein the protrusion is positioned on the proximal end of the side port to cause the sliding tab to be in a distalmost position corresponding to the closed position of the active septum valve when the slot receives the protrusion.

14. A method for obtaining a blood sample comprising:
providing an integrated intravenous (IV) catheter comprising:
a catheter adapter having a catheter that is configured to be inserted into a patient's vasculature;
a side port having a distal end by which the side port is connected to the catheter adapter, a proximal end, and a side branch, wherein the proximal end of the side port provides a first fluid pathway for drawing blood from the patient's vasculature and the side branch of the side port provides a second fluid pathway for injecting fluids into the patient's vasculature, wherein the side port further comprises an active septum valve, wherein the active septum valve comprises an actuating member and a septum, wherein the actuating member comprises a sliding tab positioned external to the side port, a septum housing positioned internal to the side port and a connecting portion that connects the sliding tab to the septum housing, wherein the septum is secured to the septum housing, wherein the active septum valve is positioned at the proximal end of the side port and includes a closed position in which the septum covers the side branch to thereby close the second fluid pathway and an open position in which the septum does not cover the side branch to thereby open the second fluid pathway, and wherein the sliding tab is configured to slide proximally relative to the side port to move the active septum valve from the closed position to the open position and to slide distally relative to the side port to move the active septum valve from the open position to the closed position; and
an extension set that is connected to the side port via the side branch;
priming the extension set while the active septum valve is in the closed position;
while the extension set is primed, obtaining a blood sample via the first fluid pathway when the active septum valve is in the closed position; and
after obtaining the blood sample, moving the active septum valve from the closed position to the open position.

15. The method of claim 14, wherein the blood sample is obtained using a blood collection set having a cannula that inserts through the septum.

16. The method of claim 14, wherein the blood sample is obtained using a blood collection adapter having a cannula that inserts through the septum.

17. The method of claim 14, further comprising:
moving the active septum valve back to the closed position; and
obtaining another blood sample while the active septum valve is in the closed position.

* * * * *